US006818566B2

(12) United States Patent
Leeson et al.

(10) Patent No.: US 6,818,566 B2
(45) Date of Patent: Nov. 16, 2004

(54) THERMAL ACTIVATION OF FLUORINE FOR USE IN A SEMICONDUCTOR CHAMBER

(75) Inventors: Noel James Leeson, Lebanon, NJ (US); Graham Hodgson, Poulton-le-Fylde (GB); Peter Harold Buckley, Salem, NH (US); Richard A. Hogle, Oceanside, CA (US)

(73) Assignee: The BOC Group, Inc., Murray Hill, NJ (US)

( * ) Notice: Subject to any disclaimer, the term of this patent is extended or adjusted under 35 U.S.C. 154(b) by 53 days.

(21) Appl. No.: 10/274,072

(22) Filed: Oct. 18, 2002

(65) Prior Publication Data

US 2004/0077162 A1 Apr. 22, 2004

(51) Int. Cl.$^7$ .............................................. H01L 21/31
(52) U.S. Cl. ........................................ 438/758; 134/1.1
(58) Field of Search ............................ 438/758; 134/1.1

(56) References Cited

U.S. PATENT DOCUMENTS

| | | | | |
|---|---|---|---|---|
| 4,615,756 A | | 10/1986 | Tsujii et al. ................. 156/345 |
| 5,297,959 A | * | 3/1994 | Hemsath ..................... 432/138 |
| 5,403,434 A | * | 4/1995 | Moslehi ....................... 134/1.2 |
| 5,797,195 A | * | 8/1998 | Huling et al. ................. 34/404 |
| 5,817,578 A | | 10/1998 | Ogawa ......................... 438/714 |
| 5,861,065 A | * | 1/1999 | Johnson ..................... 134/22.1 |
| 5,868,852 A | * | 2/1999 | Johnson et al. .............. 134/1.1 |
| 5,871,811 A | * | 2/1999 | Wang et al. ............. 427/248.1 |
| 6,022,602 A | * | 2/2000 | Nomura ..................... 428/36.8 |
| 6,095,158 A | * | 8/2000 | Shugrue ........................ 134/1 |
| 6,194,038 B1 | * | 2/2001 | Rossman ..................... 427/569 |
| 6,242,347 B1 | | 6/2001 | Vasudev et al. |
| 6,375,756 B1 | | 4/2002 | Ishibashi |
| 6,379,574 B1 | * | 4/2002 | Ou-Yang et al. ............... 216/49 |
| 6,380,103 B2 | * | 4/2002 | Gonzalez et al. ........... 438/774 |
| 6,511,608 B1 | * | 1/2003 | Mori et al. ................... 216/67 |
| 6,527,910 B2 | * | 3/2003 | Rossman ............... 156/345.43 |

FOREIGN PATENT DOCUMENTS

| | | |
|---|---|---|
| EP | 0731 497 A2 | 9/1996 |
| WO | WO 89/11905 | 12/1989 |

* cited by examiner

Primary Examiner—John F. Niebling
Assistant Examiner—Olivia T. Luk
(74) Attorney, Agent, or Firm—David A. Hey

(57) ABSTRACT

A method and system for thermally activating a oxidizing cleaning gas for use in a semiconductor process chamber cleaning process. The oxidizing cleaning gas is thermally activated by reacting the oxidizing cleaning gas with heated inert gas. The resulting thermally activated oxidizing cleaning gas does not readily deactivate, thus providing enhanced cleaning capabilities.

24 Claims, 1 Drawing Sheet

THERMAL ACTIVATION OF FLUORINE FOR USE IN A SEMICONDUCTOR CHAMBER

BACKGROUND OF THE INVENTION

1. Field of the Invention

The present invention relates generally to an apparatus for supplying gas to a semiconductor process chamber. More particularly, the present invention relates to an apparatus for supplying thermally activated fluorine or oxidizing cleaning gas to clean a semiconductor process chamber, and a process for cleaning a process chamber with the thermally activated fluorine or oxidizing cleaning gas.

2. Description of the Prior Art

A primary step in the fabrication of semiconductor devices is the formation of a thin film on a semiconductor substrate by chemical reaction of vapor precursors. A typical deposition process includes chemical vapor deposition (CVD). Conventional thermal CVD processes supply reactive gases to the substrate surface where heat-induced chemical reactions take place to form a thin film layer over the surface of the substrate being processed.

However, deposition occurs throughout the chamber, and not just on the substrate. The heaviest depositions occur in the hottest areas of the chamber, which is typically in the area of the substrate, but some deposition occurs in other areas, even fairly cool areas or areas not directly exposed to the vapor precursors, such as, chamber walls, windows, gas nozzles, tools, etc.

These depositions can cause a number of problems, such as, clogging fine holes in gas nozzles, disrupting an even flow of gas and affecting process uniformity, and clouding chamber windows affecting the ability to see into the chamber. In addition, they may form particulates, which can fall onto the substrate and cause a defect in the deposited layer or interfere with the mechanical operation of the deposition system.

To avoid such problems, the inside surface of the chamber is cleaned regularly to remove the unwanted deposition material from the chamber walls and similar areas of the processing chamber. Such cleaning procedures are commonly performed between deposition steps for every wafer or every n wafers. One type of procedure involves disassembling the chamber and cleaning each part using a solution or solvent, then drying and reassembling the system. This procedure is labor-intensive and time-consuming, reducing wafer fabrication line efficiency and increasing costs.

It is desirable to conduct the cleaning operations in-situ. Typical in-situ cleaning operations use, for example, nitrogen trifluoride ($NF_3$), molecular fluorine ($F_2$) and chlorine trifluoride ($ClF_3$) as etchant gases in cleaning operations. In these typical cleaning operations, the gas flows to the process chamber. $NF_3$ or $F_2$ is typically activated by forming a low pressure plasma by supplying an radio frequency electrical field or magnetron method in the chamber or in a remote chamber before the chamber. $ClF_3$ or $F_2$ can be introduced directly to a heated chamber but, due to the reactivity of the gas, the chamber must be cooled from its operating condition to avoid damage to the components.

U.S. Pat. No. 6,242,347 to Vasudev et al. discloses another approach to cleaning a process chamber. The disclosed method includes a brief thermal cleaning step between wafers using chlorine as the halogen cleaning gas. The chlorine gas is admitted to the chamber at an elevated temperature of about 500 to 700° F. The chlorine gas may be mixed with up to about 99.9% by volume of an inert diluent gas.

U.S. Pat. No. 6,375,756 to Ishibashi discloses a method for removing a film deposited inside a film-forming chamber. A hot element is disposed in a chamber and heated up to a temperature of 2000° C. or higher after the chamber is exhausted. Thereafter, a oxidizing cleaning gas, which is decomposed and/or activated by the hot element to generate an activated species that converts the deposited film into gaseous substance is introduced into the chamber. The oxidizing cleaning gas may be fluorine, chlorine, nitrogen trifluoride, carbon tetrafluoride, hexafluoroethane, octafluoropropane, carbon tetrachloride, pentafluorochloroethane, trifluorochlorine, trifluorochloromethane, sulfur hexafluoride, or mixtures thereof.

There are several drawbacks associated with systems using heating elements to heat oxidizing cleaning gas. In U.S. Pat. No. 6,242,347, $Cl_2$ gas is used which is not as reactive as $F_2$ or $ClF_3$ and is only suitable for deposits containing titanium. Since rapid removal of the deposits is desirable to reduce non-productive cleaning time, $F_2$ and $ClF_3$ would be more desirable cleaning agents but the heated chamber would be severely damaged at the temperatures used in this process. The less reactive $Cl_2$ is therefore used.

Another drawback is that the oxidizing cleaning gas reacts with the element in U.S. Pat. No. 6,375,756. The temperature must be carefully controlled above 2000° C. as stated in the patent to avoid reaction. As the element cools to run deposition processes, the elements is very vulnerable to attack. As a result, the element deteriorates and does not function as required. At the 2000° C. temperature, metal atoms will evaporate from the filament and deposit in the chamber thus contaminating the chamber. Also, excessive heating of a process chamber by an element located within the chamber can cause damage to components and vacuum seals within the chamber. This is illustrated by the suggestion of coating the electrical connectors with platinum to protect them from attack. This is expensive and unreliable.

SUMMARY OF THE INVENTION

A process for thermally activating an oxidizing cleaning gas comprising the steps of: (a) reacting a oxidizing cleaning gas and a preheated inert gas to form a gaseous mixture containing radicals; and (b) passing the gaseous mixture to a reaction chamber, wherein the radicals react with one or more deposits contained within the reaction chamber to form a waste gas, such as $SiF_4$, $CF_4$ or $TiF_4$.

The oxidizing cleaning gas is preferably selected from the group consisting of: fluorine, chlorine, $XeF_2$, $ClFx$, $BrFx$, (where x=1,3,5), $O_2$, $O_3$, $NF_3$, any fluorocarbon gas, other highly oxidizing or reactive gases, and any combinations thereof. The oxidizing cleaning gas is flowed to the mixing chamber at a flow rate between about 1 to 20 slpm.

The inert gas is preferably selected from the group consisting of: argon, nitrogen, helium, and any mixtures thereof. The inert gas is flowed to the mixing chamber at a flow rate between about 1 to about 20 slpm. The inert gas is preferably preheated to a temperature between about 400° C. to about 650° C.

The deposits found in the reaction chamber are typically silicon oxide, silicon nitride, polysilicon, tungsten silicide, titanium nitride, TaN, or combinations thereof, such that the waste gas is $SiF_4$, $CF_4$, $WF_6$, $TaF_5$ or $TiF_4$.

The present invention also includes a system for thermal activation of a oxidizing cleaning gas comprising: a mixing chamber which is capable of reacting a oxidizing cleaning gas and a preheated inert gas to form a gaseous mixture having radicals; and a reaction chamber for use in semiconductor processing which is in gaseous communication with the mixing chamber, wherein the radicals react with one or more deposits contained in the reaction chamber to form a waste gas.

Preferably, the oxidizing cleaning gas is fed into the mixing chamber via a fluorine feed tube which has a diameter from between about ¼ inch to about ¾ inch.

The preheated inert gas is typically fed into the mixing chamber via an inert feed tube having a diameter from between about ½ inch to about 2 inch wherein the inert feed tube comprises a packed bed of thermally conductive material, e.g., a finely divided metal. The finely divided metal is preferably selected from the group consisting of: nickel, Hastelloy, stainless steel, and any combinations thereof. Copper and aluminum alloys may also be used if there is no contamination concerns for the particular process. The inert gas feed tube further comprises a heating means, wherein the heating means surrounds the inert feed tube. The heating means is selected from the group consisting of: electrical resistance heaters, radiant heater, gas fired combustion heaters, and any combinations thereof.

The reaction chamber is constructed from an inert material selected from the group consisting of: sapphire, dense aluminum oxide, nickel, Hastelloy and any combinations thereof. The reaction chamber comprises an outer tube and a liner inserted inside the outer tube. Preferably, the reaction chamber comprises a nickel outer tube and a sapphire inner tube. The inner tube would be sealed to the outer tube at a cool region at the opposite end from the outlet of the activated gas mixture.

DETAILED DESCRIPTION OF THE INVENTION

Figure 1:
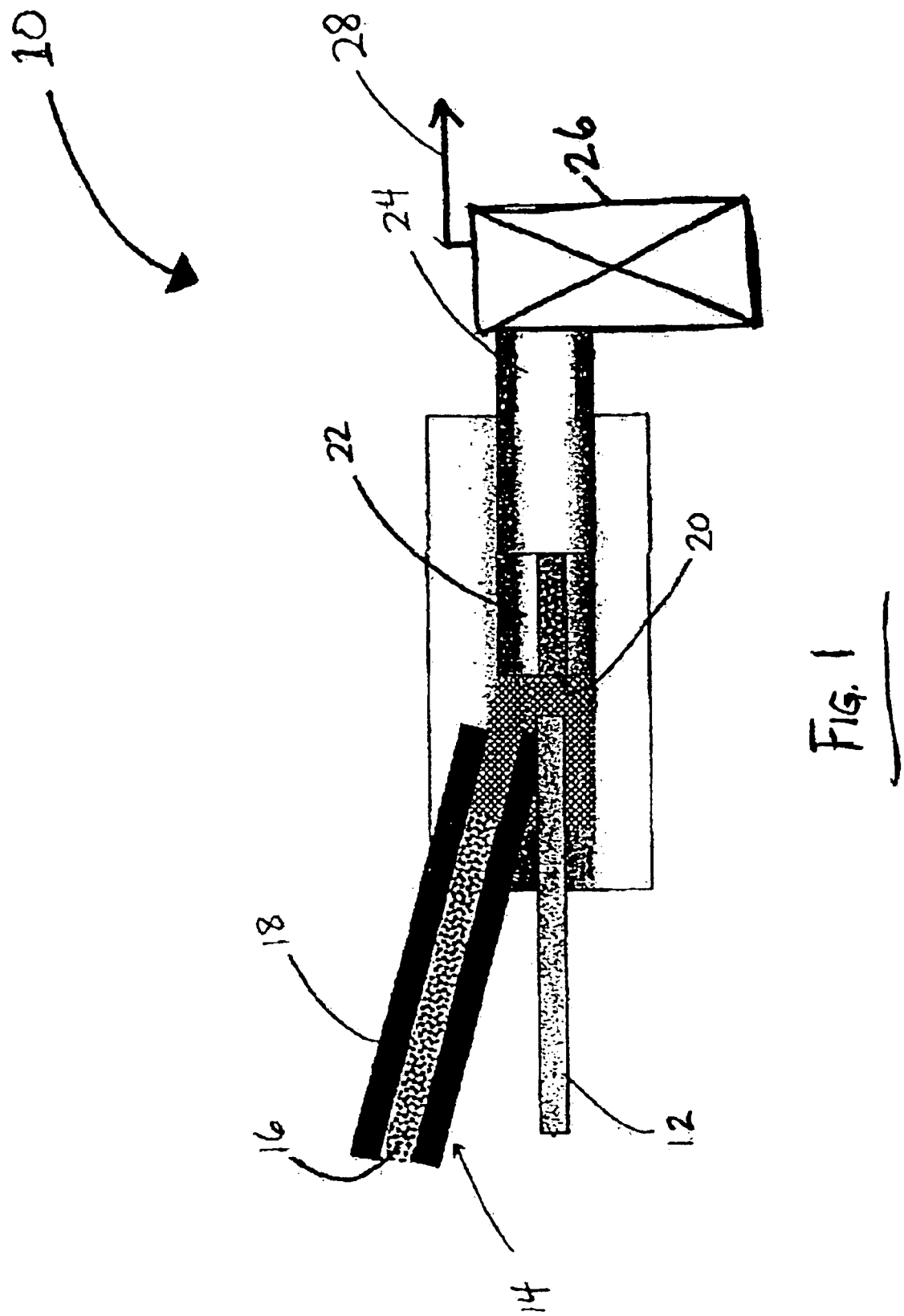
FIG. 1 illustrates a thermal activation apparatus according to the present invention.

The present invention provides a system for thermally activating a oxidizing cleaning gas for use in a cleaning process, without the use of a heating element. Mixing the oxidizing cleaning gas with heated inert gas thermally activates the oxidizing cleaning gas. The system not only eliminates the need for a heating element to contact the oxidizing cleaning gas, but also results in thermally activated gas that will not readily deactivate since it is mixed with an inert gas to keep the radical species separated.

Referring to FIG. 1, a thermal activation device for supplying thermally activated oxidizing cleaning gas to a process chamber is represented generally by reference numeral 10. Thermal activation device 10 has a oxidizing cleaning gas inlet tube 12, an inert gas inlet tube 14, mixing chamber 20, discharge tube 24 and reaction chamber 26.

The oxidizing cleaning gas is introduced into inlet tube 12. Suitable oxidizing cleaning gas for use in the present invention includes, for example, fluorine, chlorine, $XeF_2$, $ClFx$, $BrFx$, (where x=1,3,5), $O_2$, $O_3$, $NF_3$, fluorocarbon gas, other highly oxidizing or reactive gases, and any combinations thereof. Preferably, the oxidizing cleaning gas is fluorine.

Inlet tube 12 is fabricated from any suitable material capable of receiving the oxidizing cleaning gas of the present invention. Suitable material includes, for example, sapphire, dense aluminum oxide, nickel, Hastelloy, and any combination thereof.

Inlet tube 12 has a diameter of about ¼ inch to about ¾ inch. Preferably, inlet tube has a diameter about ¼ inch to about ½ inch.

Oxidizing cleaning gas is flowed through inlet tube 12 at a flow rate about 1 splm to about 20 slpm. Preferably, oxidizing cleaning gas is flowed at a flow rate about 2 slpm to about 6 slpm.

Inert gas inlet tube 14 has a packed bed 16 of finely divided metal and a heater 18, which surrounds inlet tube 14. Heater 18 heats the finely divided metal, which in turn heats the inert gas flowing through inlet tube 14. Suitable finely divided metal for use in packed bed 16 includes, for example: nickel, Hastelloy, stainless steel, and any combinations thereof. Copper and aluminum alloys may also be used if there is no contamination concerns for the particular process. Preferably, the finely divided metal is nickel.

Suitable inert gas for use in the present invention includes, for example, argon, nitrogen, helium, or any combinations thereof.

Inlet tube 14 is fabricated from any suitable material capable of carrying the inert gas to mix with the oxidizing cleaning gas of the present invention. Suitable material includes, for example: nickel, Hastelloy, stainless steel, and any combinations thereof.

Inlet tube 14 has a diameter of about ½ inch to about 2 inches. Preferably, inlet tube has a diameter about ½ inch to about 1 inch, and more preferably about ¾ inch.

Inert gas is flowed through inlet tube 14 at a flow rate about 1 slpm to about 20 slpm. Preferably, inert gas is flowed at a flow rate about 1 splm to about 10 slpm., and more preferably about 2 slpm to about 6 slpm.

Heater 18 surrounds inlet tube 14 and heats the inert gas fed through the inlet tube to a temperature about 400° C. to about 650° C. Heater 18 can be any suitable heater for use in heating inert gas flowing through inlet tube 14. Suitable heaters include, for example, electrical resistance heaters, radiant heater, gas fired combustion heaters, and any combinations thereof.

The heated inert gas from inlet tube 14 flows into mixing chamber 20 and passes around the exterior of oxidizing cleaning gas inlet tube 12. At mixing chamber 20, the heated inert gas is mixed with the oxidizing cleaning gas. The mixed gas stream then immediately flows through reaction chamber 22, which is constructed of highly inert material such as sapphire or dense aluminum oxide.

The use of inert materials, such as sapphire, to construct reaction chamber 22 is a critical aspect of the invention. Without the use of inert material, the reaction chamber can become ineffective and can result in a hazardous operation, due to the reactivity of the oxidizing cleaning gas to other materials.

Suitable inert material for constructing reaction chamber 22 includes, for example, nickel, dense aluminum oxide, sapphire, aluminum fluoride, calcium fluoride, or any combinations thereof. Preferably, reaction chamber 22 is constructed of sapphire, which is a crystal aluminum oxide material that forms an aluminum fluoride passivation layer.

In a preferred embodiment, a sapphire inner tube is sealed to the nickel outer tube at the cold inert gas purged end. This allows normal elastomer seals, such as Viton or Kalrez seals, to be used without risk of damage by the oxidizing cleaning gas.

Reaction chamber 22 is sized to ensure adequate contact between the oxidizing cleaning gas and the heated inert gas. To achieve adequate contact between the oxidizing cleaning gas and the heated inert gas, reaction chamber 22 has a diameter about ½ inch to about 1½ inches. Preferably, reaction chamber 22 has a diameter about ½ inch to about 1 inch.

The oxidizing cleaning gas, having been mixed with the high temperature inert gas, passes through a short outlet tube 24 and into the process chamber to be cleaned. Again, it is critical that outlet tube 24 is constructed from inert material to avoid reaction with the thermally activated oxidizing cleaning gas. Suitable inert material includes the same material used for constructing reaction chamber 22. Preferably, outlet tube 24 is constructed of sapphire inside of a nickel tube.

The oxidizing cleaning gas passes through process chamber 26 and reacts with one or more deposits in the process chamber. The reaction results in the formation of a waste gas that is exhausted from process chamber 26 via exhaust line 28. Deposits typically found in process chamber 26 include, for example, silicon oxide, silicon nitride, polysilicon, tungsten silicide, titanium nitride, TaN, or combinations thereof. The waste gas is typically $SiF_4$, $CF_4$, $WF_6$, $TaF_5$ or $TiF_4$, when fluorine is employed as an oxidizing cleaning gas.

In this process, several possible chemical reactions can occur. If inert gases such as helium or nitrogen are used, and the oxidizing cleaning gas is fluorine, the reaction will tend to form fluorine radicals. Fluorine will split into a highly reactive and very oxidizing condition where the fluorine element forms a radical. Due to the dilution provided by the inert gas, these radicals now cannot recombine with each other until sufficient mixing occurs. This will maintain the reactivity of this mixture for some period of time as it passes through the process chamber and reacts with the desired deposits.

If argon is used as the inert gas and fluorine is used as the oxidizing cleaning gas, an intermediate compound [$ArF_x$] may be formed. This is a metastable compound that will readily give off the fluorine radicals as it passes into the process chamber to be cleaned. The argon fluoride may stabilize the active fluorine for a longer period of time, and therefore, may be useful in this process to sustain the fluorine in an active state. Maximizing the argon fluoride will depend on the relative argon flow rates and the appropriate temperature of the mixing chamber.

In all cases, with respect to fluorine, the fluorine can be generated in an electrolytic fluorine generator, since fluorine stored in cylinders is impractical. The inert gas is supplied from compressed gas cylinders or bulk storage systems.

Overall, by using the apparatus of the present invention, the thermal cleaning process has the potential for converting a higher percentage of the molecular fluorine into fluorine radicals. This is due to the fact that the thermal energy is present in the entire reaction chamber, rather than being concentrated to a "corona-like" discharge, and the entire flow of fluorine would be in contact with this high temperature inert gas. The inert gas itself, once the fluorine has split into radicals, keeps these species separated allowing the radicals to pass into the chamber in need of cleaning, without recombination to form molecular fluorine.

Another advantage of the present invention is that elemental fluorine is less expensive than other traditionally used oxidizing cleaning gases, such as $NF_3$. The thermal activation system of the present invention allows for the lower cost fluorine generation to provide necessary reactants to clean chambers with a considerable lower cost-of-ownership for the equipment user.

It should be understood that the foregoing description is only illustrative of the present invention. Various alternatives and modifications can be devised by those skilled in the art without departing from the invention. Accordingly, the present invention is intended to embrace all such alternatives, modifications and variances.

What is claimed is:

1. A process for thermally activating an oxidizing cleaning gas comprising the steps of:
    (a) reacting an oxidizing cleaning gas and a preheated inert gas to form a gaseous mixture having one or more radicals; and
    (b) passing said gaseous mixture to a reaction chamber, wherein said one or more radicals react with one or more deposits contained within said reaction chamber to form a waste gas.

2. The process of claim 1, wherein said oxidizing cleaning gas is selected from the group consisting of: fluorine, chlorine, $XeF_2$, ClFx, BrFx, $O_2$, $O_3$, $NF_3$, fluorocarbon gas, and any combinations thereof.

3. The process of claim 1, wherein said oxidizing cleaning gas is flowed to said mixing chamber at a flow rate between about 1 slpm to about 20 slpm.

4. The process of claim 1, wherein said inert gas is selected from the group consisting of: argon, nitrogen, helium, and any mixtures thereof.

5. The process of claim 1, wherein said inert gas is flowed to said mixing chamber at a flow rate between about 1 slpm to about 20 slpm.

6. The process of claim 1, wherein said inert gas is preheated to a temperature between about 250° C. to about 800° C.

7. The process of claim 1, wherein said one or more deposits are selected from the group consisting of: silicon oxide, silicon nitride, polysilicon, tungsten silicide, titanium nitride, TaN, and any combinations thereof.

8. The process of claim 1, wherein said waste gas is at least one selected from the group consisting of: $SiF_4$, $CF_4$, $WF_6$, $TaF_5$, and $TiF_4$.

9. A system for thermal activation of an oxidizing cleaning gas comprising:
    (a) a mixing chamber which is capable of reacting an oxidizing cleaning gas and a preheated inert gas to form a gaseous mixture having one or more radicals; and
    (b) a reaction chamber for use in semiconductor processing which is in gaseous communication with said mixing chamber, wherein said one or more radicals react with one or more deposits contained within said reaction chamber to form a waste gas.

10. The system of claim 9, wherein said oxidizing cleaning gas is selected from the group consisting of: fluorine, chlorine, $XeF_2$, ClFx, BrFx, $O_2$, $O_3$, $NF_3$, fluorocarbon gas, and any combinations thereof.

11. The system of claim 9, wherein said oxidizing cleaning gas is fed to said mixing chamber via a feed tube which has a diameter from between about ¼ inch to about 1 inch.

12. The system of claim 9, wherein said inert gas is selected from the group consisting of: argon, nitrogen, helium, and any mixtures thereof.

13. The system of claim 9, wherein said preheated inert gas is fed to said mixing chamber via an inert gas feed tube having a diameter from between ½ inch to about 2 inches.

14. The system of claim 13, wherein said inert gas feed tube comprises a packed bed of thermally conductive material.

15. The system of claim 14, wherein said thermally conductive material is a finely divided metal.

16. The system of claim 15, wherein said finely divided metal is selected from the group consisting of: nickel, Hastelloy, stainless steel, copper alloy, aluminum alloy, and any combinations thereof.

17. The system of claim 13, wherein said inert gas feed tube further comprises a heating means.

18. The system of claim 17, wherein said heating means surrounds said inert feed tube.

19. The system of claim 17, wherein said heating means is selected from the group consisting of: electrical resistance heaters, radiant heater, gas fired combustion heaters, and any combinations thereof.

20. The system of claim 9, wherein said reaction chamber is constructed from an inert material.

21. The system of claim 20, wherein said inert material is selected from the group consisting of: nickel, dense aluminum oxide, sapphire, aluminum fluoride, calcium fluoride, and any combinations thereof.

22. The system of claim 9, wherein said reaction chamber comprises an outer tube and a liner inserted inside the outer tube.

23. The system of claim 22, wherein said reaction chamber comprises a nickel outer tube and a sapphire liner.

24. The system of claim 9, wherein said waste gas is at least one selected from the group consisting of: $SiF_4$, $CF_4$, $WF_6$, $TaF_5$, and $TiF_4$.

* * * * *